United States Patent
Tjon

(10) Patent No.: US 10,945,794 B2
(45) Date of Patent: *Mar. 16, 2021

(54) COMPUTER-AIDED DESIGN AND PREPARATION OF BONE GRAFT

(71) Applicant: Kristian Tjon, Santa Ana, CA (US)

(72) Inventor: Kristian Tjon, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/011,892

(22) Filed: Sep. 3, 2020

(65) Prior Publication Data

US 2020/0397508 A1 Dec. 24, 2020

Related U.S. Application Data

(62) Division of application No. 16/411,480, filed on May 14, 2019, now Pat. No. 10,799,295.

(60) Provisional application No. 62/837,644, filed on Apr. 23, 2019.

(51) Int. Cl.
| | |
|---|---|
| *A61B 34/10* | (2016.01) |
| *A61F 2/30* | (2006.01) |
| *A61F 2/28* | (2006.01) |

(52) U.S. Cl.
CPC ............ *A61B 34/10* (2016.02); *A61F 2/2803* (2013.01); *A61F 2/30942* (2013.01); *A61B 2034/105* (2016.02); *A61F 2002/30948* (2013.01); *A61F 2240/002* (2013.01)

(58) Field of Classification Search
CPC .......... A61B 34/10; A61F 2/28; A61F 2/2803; A61F 2/30; A61F 2/30942
See application file for complete search history.

(56) References Cited

U.S. PATENT DOCUMENTS 9,411,939 B2  8/2016  Furrer et al.
10,799,295 B1 * 10/2020 Tjon ..................... A61B 34/10

OTHER PUBLICATIONS

Amin, "Block Bone Graft for Dental Implants 2015 Update-Ramsey Amin DDS Reviews", Blog, https://www.BurbankDentalImplants.com, Feb. 2015.
Garagiola et al., "Computer-aided design/computer-aided manufacturing of hydroxyapatite scaffolds for bone reconstruction in jaw-bone atrophy: a systematic review and case report", Maxillofacial Plastic and Reconstructive Surgery, 38(2), 1-9, 2016, DOI: 10.1186/s40902-015-0048-7.
Kumar et al., "Bone grafts in dentistry", Journal of Pharmacy & BioAllied Sciences, 5(Suppl 1), S125-S127, Jun. 2013, DOI: 10.4103/0975-7406.113312: 10.4103/0975-7406.113312.
Mirković et al., "Application of modem computer-aided technologies in the production of individual bone graft: A case report", Vojnosanit Pregl, 72(12), 1126-1131, 2015, DOI: 10.2298/VSP140915117M.
Straumann, "A New Perspective of Bone Augmentation", straumanngroup.us/eShop or straumanngroup.ca/eShop, 2018.

* cited by examiner

*Primary Examiner* — Christopher J Beccia
(74) *Attorney, Agent, or Firm* — Maschoff Brennan; Brent A. Johnson; Yuefen Zhou

(57) ABSTRACT

Described herein is a method of preparing a bone graft product, comprising computer-guided precision cutting an unshaped piece of bone from a human cadaver or a bovine animal to provide a shaped piece of bone having a predetermined shape that is determined by a human being using computer-aided design. Bone graft products prepared using this method and methods of grafting these products are also disclosed.

16 Claims, No Drawings

COMPUTER-AIDED DESIGN AND PREPARATION OF BONE GRAFT

CROSS-REFERENCE TO RELATED APPLICATIONS

This application is a division of U.S. patent application Ser. No. 16/411,480, filed May 14, 2019; which claims the benefit of U.S. provisional Pat. App. No. 62/837,644, filed Apr. 23, 2019; all of which are incorporated by reference herein in their entirety.

BACKGROUND

Conventionally, to place a dental implant, a sufficient volume of bone is needed to surround an implant site. If the bone is insufficient, bone graft may need to be placed before implant can occur. The bone used in the graft, especially for a small graft site, is usually a ground particulate derived from human cadaver or bovine bone. The bone particulate is a substance that resembles in size to sands of varying grain size.

For a large graft site, a large volume of graft particulate is needed. Maintaining the graft shape and size is difficult during the long healing phase after the area is sutured close. Traditionally, the shape of the graft is typically maintained with a moldable titanium mesh which is cut to size, curved to achieve the desired shape of bone graft, and fixed in place with screws onto a jaw bone of a patient. This is very technique sensitive and time consuming.

SUMMARY

Disclosed herein is a bone graft that is generated using computer-aided design (CAD) and manufactured directly from a piece of human cadaver bone or a piece of bovine bone with computer-guided precision-cut in the desired three dimensional shape and size, and is sterile, sealed in sterile packaging, and ready for a surgeon for direct placement .

Some embodiments include a method of preparing a bone graft product, comprising computer-guided precision cutting an unshaped piece of bone from a human cadaver or a bovine animal to provide a shaped piece of bone having a predetermined shape that is determined by a human being using computer-aided design.

Some embodiments include a bone graft product comprising: the shaped piece of bone referred to above and/or described herein and a sterile packaging containing the shaped piece of bone.

Some embodiments include a method of grafting bone in a human being comprising, bolting the shaped piece of bone referred to above and/or described herein to a bone at an intended graft site of a human being.

DETAILED DESCRIPTION

In general, data from computed tomographic (CT) scan can be used to shape precisely a piece of bone using a computer-aided design (CAD) and computer-aided manufacture to generate a bone graft to a desired shape and size. The shaped piece of bone can then be inserted into the bone defect. After a few months of healing, an implant can then be placed in the bone graft site.

Specifically, shaped piece of bone for the bone graft is generated by the following steps. First, the 3D shape of the existing bone at the recipient site to be grafted of a human being is obtained with a CT scan.

Second, computer software accepts the CT scan data. An interface with the software allows a human user to determine and input the desired shape of the bone that the grafting procedure is intended to achieve. The information from the CT scan and the input from the human user are used to create a digital model of the desired bone graft. Thus, the computer software assists the human user in determining the shape of a bone graft that will fit into the defect and provide desired external contour of the bone after graft is done.

Third, the computer software directs a cutting unit, such as a milling unit, to shape a piece of human cadaver or bovine bone into the shape of the digital model to generate a bone graft of the desired shape.

Fourth, the shaped piece of bone or bone graft is sterilized and sealed in sterile packaging, and is ready to be sent to a surgeon for placement.

The shape of the bone graft can be modified by the user using 3D computer modeling based on the CT data of the patient to create any sort of external contour. The flexibility of the shape so designed also allow for the bone graft to fit onto the bone graft site of a recipient with varying relief to allow for fine tuning with granular graft material. The bone graft can be drilled to create pre-drilled holes that allows to fix it onto a bone graft site with surgical screws.

Computed Tomography (CT) Scan

The term "computed tomography," or CT, refers to a computerized X-ray imaging procedure in which a narrow beam of X-rays is aimed at a patient and quickly rotated around a targeted site, producing signals that are processed by the machine's computer to generate cross-sectional images—or "slices"—of the targeted site. These slices are called tomographic images and contain more detailed information than conventional X-rays. Once a number of successive slices are collected by the machine's computer, they can be digitally "stacked" together to form a three-dimensional image of the patient that allows for easier identification and location of basic structures, and etc.

Thus, by using a CT scan, the 3D shape of the existing bone at the recipient site to be grafted of a patient can be obtained. The size and shape of defect of the bone or a "missing bone" at the recipient site for grafting can be clearly seen.

Computer-Aided Design (CAD)

The above CT images are the basis for the computer-aided 3D graft modeling. Computer software can be used to accept the CT scan data in DICOM (Digital Imaging and Communications in Medicine) format to generate a 3D model of the existing targeted bone area. After generating the 3D model, input parameters, such as shape and size of the bone graft and its position in the targeted bone area, are defined to generate the desired shape of the bone after grafting is done. This graft modeling process allows a surgeon to digitally create a 3D model of a desired bone graft that will fit into the defect very well, recreating the desired external contour of the bone after graft is done. The 3D bone graft model thus created would satisfy medicoesthetic, technical, and functional requirements.

The process of designing the 3D graft model is carried out taking into consideration the performance of the equipment for graft manufacturing and the minimum required cross-sectional graft thickness of 3 mm. A graft having a cross-sectional thickness less than 3 mm may result in undesirable mechanical properties. For example, a graft which is too thin may cause graft placement into the jaw be compromised by potential breakage of the graft while positioning and fixing it with appropriate screws.

In some embodiments, the 3D graft model is fitted together with the 3D model of the existing bone of the intended graft site and an implant model (or multiple implant models) using computer software. During this process, geometric characteristics of the bone graft are analyzed, as well as its position in the intended bone graft site in relation to the implant (or multiple implants). Additionally, a final check-up of the following parameters: cross-sections of the graft; maximum dimensions (length, width, height); minimum graft wall thickness; negative angles of the graft; and sharp edges is conducted to make sure that a desired fit can be achieved.

In some embodiments, after satisfying all virtual, esthetic, and functional requirements, the graft model may be manufactured along with the intended graft area by applying the rapid prototyping (RP) technology, such as 3D printing, to generate physical models. These physical models allow users, such as surgeons, to hold, analyze, inspect, the model prior to final fabrication, which enables identification and elimination of some potential problems that are not visible in the virtual 3D model. Then, the original 3D graft model can be modified and corrected to generate the final version of the graft 3D model that is ready for fabrication of actual bone graft.

The unshaped piece of bone includes any piece of bone from a human cadaver or a bovine animal that has not been processed or shaped in any way except to cut or break the piece of bone from the cadaver or animal. The shaped piece of bone is an intact fragment of human cadaver or bovine bone, except for the fact that the piece of bone has been removed from the human cadaver or bovine animal and shaped as described herein. Synthetic materials or solids formed from particulate bone material are not part of the piece of bone, although they could potentially be added to make fine adjustments after the piece of bone is grafted into the graft recipient.

Generally, the desired shape of the piece of bone to be used in the bone graft is achieved by shaping, e.g. by milling or cutting, an unshaped piece of bone from a human cadaver or a bovine animal to a predetermined shape, size, and volume.

Based on the conformation of the final 3D graft model of the desired bone graft described herein, a milling machine unit, or other suitable cutting or shaping device, may be directed or controlled by the proprietary computer software to precision-cut a piece of a human cadaver bone or bovine bone to generate a shaped piece of actual bone graft with desired shape and dimensions. CAD methods may also be applied to other shaping methods, such as other cutting methods.

The shape of the shaped piece of bone created herein may have any sort of external contour, determine by human user. The flexibility of the shape allows the graft to fit onto the bone graft site of a recipient with varying relief to allow for fine tuning with granular graft material.

In some embodiments, the shaped piece of bone can be drilled to create pre-drilled holes that allows to fix it onto a bone graft site with surgical screws. These pre-drilled holes can have desired shape and size for various applications.

Except for the fact that it has been removed from the human cadaver or bovine animal and shaped for a bone graft, the shaped piece of bone should be in the same form as a whole bone in term of characteristic of the bone, such as bone property and bone density, and not a piece of processed bone material. The shaped piece of bone should be a shape and volume to serve its intended purpose in the bone graft, and constitute a substantial majority of the bone graft volume. In some embodiments, the shaped piece of bone is at least about 70%, at least about 80%, at least about 90%, at least about 95%, or at least about 90% of the volume of the bone graft. In some embodiments, the shaped piece of bone has a volume of at least about 0.01 cubic centimeter (cc), at least about 0.1 cc, at least about 0.2 cc, at least about 0.3 cc, at least about 0.4 cc, at least about 0.5 cc, at least about 0.6 cc, at least about 0.7 cc, at least about, 0.8 cc, at least about 0.9 cc, at least about 1 cc, at least about 2 cc, at least about 3 cc, at least about 4 cc, at least about 5 cc, at least about 6 cc, at least about 7 cc, at least about, 8 cc, at least about 9 cc, at least about 10 cc, about 0.01-1000 cc, about 0.01-0.1 cc, about 0.1-0.2 cc, about 0.2-0.3 cc, about 0.3-0.4 cc, about 0.4-0.5 cc, about 0.5-0.6 cc, about 0.6-0.7 cc, about 0.7-0.8 cc, about 0.8-0.9 cc, about 0.9-1 cc, about 1-2 cc, about 2-3 cc, about 3-4 cc, about 4-5 cc, about 5-6 cc, about 6-7 cc, about 7-8 cc, about 8-9 cc, about 9-10 cc, about 10-20 cc, about 20-30 cc, about 30-40 cc, about 40-50 cc, about 50-60 cc, about 60-70 cc, about 70-80 cc, about 80-90 cc, about 90-100 cc, about 100-200 cc, about 200-300 cc, about 300-400 cc, about 400-500 cc, about 500-600 cc, about 600-700 cc, about 700-800 cc, about 800-900 cc, about 900-1000 cc, about 0.01-0.5 cc, about 0.5-1 cc, about 1-5 cc, about 5-10 cc, about 10-50 cc, about 50-100 cc, about 100-500 cc, or about 500-1000 cc.

The shaped piece of bone may further comprise preformed (e.g. drilled) holes that are suitable for fixing the shaped piece of bone into place with surgical screws. For example, the shaped piece of bone may contain 1, 2, 3, 4, 5, 6, 7, 8, 9, or 10 holes of the appropriate size for use with a surgical screw. The holes may have a diameter, for example of about 0.1-10 mm, about 0.1-3 mm, about 3-7 mm, about 7-10 mm, about 0.1-1 mm, about 0.1-1.5 mm, about 1.5-2 mm, about 2-2.5 mm, about 2.5-3 mm, about 3-4 mm, about 4-5 mm, about 5-7 mm, or about 7-10 mm. The holes may have any suitable length for surgical screws, such as about 0.1-50 mm, about 0.9-1 cc, about 1-2 mm, about 2-3 mm, about 3-4 mm, about 4-5 mm, about 5-6 mm, about 6-7 mm, about 7-8 mm, about 8-9 mm, about 9-10 mm, about 10-12 mm, about 12-14 mm, about 14-16 mm, about 16-18 mm, about 18-20 mm, about 1-5 mm, about 5-10 mm, about 10-15 mm, or about 15-20 mm.

The shaped piece of bone can have any suitable shape for a bone graft. For example, it may be shaped so that it is suitable for a bone graft for a dental implant, a bone graft for cosmetic plastic surgery, a bone graft for post-cancer reconstructive surgery, or adjunct bone augmentation for orthopedic surgery. In some embodiments, the piece of bone is shaped so that it is suitable for a bone graft for a dental implant. In some embodiments, the piece of bone is shaped so that it is suitable for a bone graft for cosmetic plastic surgery. In some embodiments, the piece of bone is shaped so that it is suitable for a bone graft for post-cancer reconstructive surgery. In some embodiments, the piece of bone is shaped so that it is suitable for an adjunct bone augmentation for orthopedic surgery.

Upon finishing, the shaped piece of bone or bone graft is sterilized. For example, ethylene oxide can be used for sterilization of the shaped piece of bone. The sterilized shaped piece of bone or bone graft is then sealed in a sterile package, which is ready to be sent to users, such as surgeons, for direct placement at intended bone graft site.

The shaped piece of bone or bone graft is bolted to the bone at an intended graft site. In some embodiments, the shaped piece of bone or bone graft with predrilled holes can be easily attached to the bone at a graft site using surgical screws.

A graft enhancing agent may be used, either around the time of the attachment of the bone graft to the bone at the graft site, sometime after attachment, or later during healing, to enhance healing and integration of the shaped piece of bone or bone graft to the bone at the graft site.

For example, the graft enhancing agent may be applied to the bone at the graft site just prior to attaching the bone graft. Alternatively or additionally, the graft enhancing agent may be applied to both the host bone at the graft site and the bone graft just after attaching the bone graft.

The graft enhancing agent may also be combined with the shaped piece of bone or bone graft in the sterilized packaging. For example, the surface of the graft enhancing agent intended to come into contact with the bone at the graft site may have a graft enhancing agent on the surface or permeating the surface. Part (such as the surface intended to come in contact with the bone at the graft site) or all of the shaped piece of bone could be submerged in a solution or suspension containing the graft enhancing agent. The bone graft may then be removed from the solution or suspension, and then either applied to the bone at the graft site or placed in the sterile packaging.

The graft enhancing agent could be any substance that enhances wound healing, enhances bone growth, or otherwise helps to enhance healing and/or integration of the bone graft to the bone at the graft site. Examples of suitable graft enhancing agents include blood-derived agents or bone-derived agents such as growth factors, including human platelet derived growth factor (hPDGF) such as recombinant PDGF (rhPDGF), e.g. Gem-21S; bone morphogenic protein 2 (BMP-2); stromal cell-derived factor 1 (SDF-1); calcium-based agents such as a calcium phosphate ceramic; etc.

In some embodiments, the graft enhancing agent is prepared and/or isolated directly from the patient's blood which is withdrawn from the patient during the procedure of attaching the bone graft to the bone at the graft site. In some embodiments, such a graft enhancing agent is applied at the graft site at the time of attaching the bone graft to the bone at the graft site. In some embodiments, preparation and isolation of a graft enhancing agent, attachment of the bone graft to the bone at the graft site, and application of the graft enhancing agent may be done in one procedure during one visit of the patient.

Any suitable amount of graft enhancing agent (such as hPDGF, rhPDGF, BMP-2, SDF-1, a or calcium phosphate ceramic) may be used, for example, the amount of the graft enhancing agent on or in the bone graft, or administered to the graft site (on the recipient bone, on the graft bone, and/or on surrounding tissue may be about 0.01 µg-1,000 mg, about 0.01-1000 µg, about 0.01-0.1 µg, about 0.1-0.2 µg, about 0.2-0.3 µg, about 0.3-0.4 µg, about 0.4-0.5 µg, about 0.5-0.6 µg, about 0.6-0.7 µg, about 0.7-0.8 µg, about 0.8-0.9 µg, about 0.9-1 µg, about 1-2 µg, about 2-3 µg, about 3-4 µg, about 4-5 µg, about 5-6 µg, about 6-7 µg, about 7-8 µg, about 8-9 µg, about 9-10 µg, about 10-20 µg, about 20-30 µg, about 30-40 µg, about 40-50 µg, about 50-60 µg, about 60-70 µg, about 70-80 µg, about 80-90 µg, about 90-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 1,000-2,000 µg, about 2,000-3,000 µg, about 3,000-4,000 µg, about 4,000-5,000 µg, about 5,000-6,000 µg, about 6,000-7,000 µg, about 7,000-8,000 µg, about 8,000-9,000 µg, about 9,000-10,000 µg, about 0.01-0.5 µg, about 0.5-1 µg, about 1-5 µg, about 5-10 µg, about 10-50 µg, about 50-100 µg, about 100-500 µg, about 500-1000 µg, about 1-5 mg, about 5-10 mg, about 10-100 mg, about 100-200 mg, about 200-300 mg, about 300-400 mg, about 400-500 mg, or about 500-1,000 mg.

Fine adjustments can be made to the shape of the shaped piece of bone or bone graft after it is grafted onto the bone of the graft site. In some embodiments, fine adjustments are made to the shape of the shaped piece of bone or bone graft by cutting or milling. In some embodiments, fine adjustments are made to the shape of the shaped piece of bone or bone graft after it is attached to the bone of the graft site by adding granular graft material.

A bone graft product described herein can be potentially customized to each patient and for each type of clinical situation. The bone graft product well matches the shape of the bone defect and can be easily implanted during surgery. This matching of the shape can help to reduce the time for the surgical operation, improves the precision in adapting the graft, which may improve its integration with the surrounding bone of a patient, and contribute to the good healing of the defects. Thus, the bone graft product described herein can potentially have very broad applications, for example, in dentistry, cosmetic plastic surgery, post-cancer reconstructive surgery, adjunct bone augmentation for orthopedic surgery, or other types of custom bone-repair, without the use of fillers or artificial materials.

Specifically Contemplated Embodiments

The following are examples of embodiments that are specifically contemplated by the inventor:

Embodiment 1. A method of preparing a bone graft product, comprising computer-guided precision cutting an unshaped piece of bone from a human cadaver or a bovine animal to provide a shaped piece of bone having a predetermined shape.

Embodiment 2. The method of embodiment 1, wherein the predetermined shape is determined based on the difference between the three dimensional shape of the bone at an intended graft site of a human being and the desired shape of the bone at the intended graft site of the human being after the graft is completed.

Embodiment 3. The method of embodiment 2, wherein the three dimensional shape of the bone at the intended graft site is obtained by computed tomography scan.

Embodiment 4. The method of embodiment 1, 2, or 3, wherein the predetermined shape is determined by a human being using computer-aided design.

Embodiment 5. The method of embodiment 1, 2, 3, or 4, wherein the predetermined shape is designed using a 3D-modeling software.

Embodiment 6. The method of embodiment 1, 2, 3, 4, or 5, wherein the shaped piece of bone is manufactured by a process comprising use of a computer-guided milling machine unit.

Embodiment 7. A bone graft product comprising:
  the shaped piece of bone of claim 1, 2, 3, 4, 5, or 6; and
  a sterile packaging containing the shaped piece of bone.

Embodiment 8. The bone graft product of embodiment 7, wherein the shaped piece of bone has a volume of at least 0.1 cc.

Embodiment 9. The bone graft product of embodiment 7 or 8, wherein the shaped piece of bone has a shape that is suitable for a bone graft to be made in preparation for a dental implant.
Embodiment 10. The bone graft product of embodiment 7 or 8, wherein the shaped piece of bone has a shape that is suitable for cosmetic plastic surgery.
Embodiment 11. The bone graft product of embodiment 7 or 8, wherein the shaped piece of bone has a shape that is suitable for post-cancer reconstructive surgery,
Embodiment 12. The bone graft product of embodiment 7 or 8, wherein the shaped piece of bone has a shape that is suitable for adjunct bone augmentation for orthopedic surgery.
Embodiment 13. The bone graft product of embodiment 7, 8, 9, 10, 11, or 12, wherein the shaped piece of bone further comprises pre-formed holes that are suitable for fixing the piece of bone into a place with surgical screws.
Embodiment 14. The bone graft product of embodiment 7, 8, 9, 10, 11, 12, or 13, wherein the thickness of the shaped piece of bone is no less than 3 mm.
Embodiment 15. The bone graft product of embodiment 7, 8, 9, 10, 11, 12, 13, or 14, further comprising a graft enhancing agent.
Embodiment 16. A method of grafting bone in a human being comprising, bolting the shaped piece of bone of embodiment 7, 8, 9, 10, 11, 12, 13, 14, or 15 to a bone at an intended graft site of a human being.
Embodiment 17. The method of embodiment 16, wherein fine adjustments are made to the shape of the shaped piece of bone is grafted to the intended graft site.
Embodiment 18. The method of embodiment 17, wherein fine adjustments are made to the shape of the shaped piece of bone by cutting the shaped piece of bone.
Embodiment 19. The method of embodiment 17 or 18, wherein fine adjustments are made to the shape of the shaped piece of bone by adding granular graft material.
Embodiment 20. The method of embodiment 16, 17, 18, or 19, wherein a graft enhancing agent is applied to the shaped piece of bone, the bone at the intended graft site, or tissue surrounding the bone at the intended graft site, or a combination thereof.

What is claimed is:

1. A bone graft product suitable for use in a human being in need thereof comprising:
    a shaped piece of bone; and
    a sterile packaging containing the shaped piece of bone,
    wherein the shaped piece of bone is prepared by using computer-guided precision cutting an unshaped piece of bone from a human cadaver or a bovine animal, and the shaped piece of bone having a predetermined shape that is determined using computer-aided design,
    wherein the predetermined shape is determined based on the difference between the three dimensional shape of the bone at an intended graft site of the human being and the desired shape of the bone at the intended graft site of the human being after the graft is completed,
    wherein the shaped piece of bone has a desired shape and size that fits in the intended graft site precisely when inserted into the bone defect,
    wherein no part of the bone at the intended graft site is removed from the human being, and
    wherein the unshaped piece of bone comprises any piece of bone from a human cadaver or a bovine animal that was not prepared by combining smaller pieces of bones.

2. The bone graft product of claim 1, wherein the three dimensional shape of the bone at the intended graft site is obtained by computed tomography scan.

3. The bone graft product of claim 1, wherein the predetermined shape of the bone graft is designed using a 3D-modeling software.

4. The bone graft product of claim 1, wherein the shaped piece of bone is manufactured by a process comprising the use of a computer-guided milling machine unit.

5. The bone graft product of claim 1, wherein the shaped piece of bone has a volume of at least 0.1 cc.

6. The bone graft product of claim 1, wherein the shaped piece of bone further comprises pre-formed holes that are suitable for fixing the shaped piece of bone into the intended graft site with surgical screws.

7. The bone graft product of claim 1, wherein the thickness of the shaped piece of bone is no less than 3 mm.

8. The bone graft product of claim 1, wherein the shaped piece of bone is customized to the human being.

9. The bone graft product of claim 1, wherein the shaped piece of bone is suitable to be bolted to a bone at the intended graft site of the human being.

10. The bone graft product of claim 1, further comprising a graft enhancing agent.

11. The bone graft product of claim 10, wherein the graft enhancing agent is applied to the shaped piece of bone, the bone at the intended graft site, or tissue surrounding the bone at the intended graft site, or a combination thereof, when grafting the shaped piece of bone.

12. The bone graft product of claim 1, wherein the shaped piece of bone has a shape that is suitable for cosmetic plastic surgery.

13. The bone graft product of claim 1, wherein the shaped piece of bone has a shape that is suitable for post-cancer reconstructive surgery.

14. The bone graft product of claim 1, wherein the shaped piece of bone has a shape that is suitable for adjunct bone augmentation for orthopedic surgery.

15. The bone graft product of claim 1, wherein the shaped piece of bone has a shape that is suitable for dental implant.

16. The bone graft product of claim 1, wherein the shaped piece of bone is ready for direct placement at the intended bone graft site.

* * * * *

UNITED STATES PATENT AND TRADEMARK OFFICE
CERTIFICATE OF CORRECTION

| | |
|---|---|
| PATENT NO. | : 10,945,794 B2 |
| APPLICATION NO. | : 17/011892 |
| DATED | : March 16, 2021 |
| INVENTOR(S) | : Kristian Tjon |

It is certified that error appears in the above-identified patent and that said Letters Patent is hereby corrected as shown below:

In the Claims

Column 7, Line 51, Claim 1, please replace "having" with -- has --

Signed and Sealed this
Twenty-sixth Day of April, 2022

*Katherine Kelly Vidal*

Katherine Kelly Vidal
*Director of the United States Patent and Trademark Office*